(12) United States Patent
Glaven et al.

(10) Patent No.: US 11,881,606 B2
(45) Date of Patent: Jan. 23, 2024

(54) CONDUCTIVE MATERIALS TO DRIVE BACTERIAL CARBON DIOXIDE FIXATION

(71) Applicant: The Government of the United States of America, as represented by the Secretary of the Navy, Arlington, VA (US)

(72) Inventors: Sarah M. Glaven, Washington, DC (US); Lina Bird, Washington, DC (US); Leonard M. Tender, Bethesda, MD (US)

(73) Assignee: The Government of the United States of America, as repersented by the Secretary of the Navy, Arlington, VA (US)

( * ) Notice: Subject to any disclaimer, the term of this patent is extended or adjusted under 35 U.S.C. 154(b) by 388 days.

(21) Appl. No.: 17/116,830

(22) Filed: Dec. 9, 2020

(65) Prior Publication Data
US 2021/0273250 A1  Sep. 2, 2021

Related U.S. Application Data

(60) Provisional application No. 62/947,327, filed on Dec. 12, 2019.

(51) Int. Cl.
| | | |
|---|---|---|
| *G01N 27/28* | (2006.01) | |
| *H01M 8/16* | (2006.01) | |
| *C12M 1/12* | (2006.01) | |
| *C02F 11/02* | (2006.01) | |
| *C02F 3/34* | (2023.01) | |

(52) U.S. Cl.
CPC ............... *H01M 8/16* (2013.01); *C02F 3/34* (2013.01); *C02F 11/02* (2013.01); *C12M 25/08* (2013.01)

(58) Field of Classification Search
CPC . Y02E 60/50; Y02E 50/10; B01L 2300/0645; C02F 2103/08; C02F 2001/46138; C02F 3/005; G01N 27/28; G01N 27/327; G01N 27/4161; H01M 8/16
USPC ......................................................... 435/135
See application file for complete search history.

(56) References Cited

U.S. PATENT DOCUMENTS

2018/0245108 A1    8/2018   Reed et al.

OTHER PUBLICATIONS

Erable et al., ( Bioelectrochemistry 2009, 78, pp. 51-56.*
Malanoski et al. ( Microbial Biotechnol. 2017, pp. 1-14.*
Jansen et al. ( Hindawi 2013, p. 1-13.*
Rau, G.H. "The race to remove CO2 needs more contestants." Nat. Clim. Chang. 9, 256 (2019).
Onderko et al. "Electrochemical Characterization of Marinobacter atlanticus Strain CP1 Suggests a Role for Trace Minerals in Electrogenic Activity" Front. Energy Res., Jun. 26, 2019.
Bird, Lina J., et al. "Engineered living conductive biofilms as functional materials." MRS Communications 9.2 (2019): 505-517.
Yates et al., "Toward understanding long-distance extracellular electron transport in an electroautotrophic microbial community" Energy Environ. Sci., 2016,9, 3544-3558.
Florian et al., "Electroactive Bacteria Associated With Stainless Steel Ennoblement in Seawater." Front. Microbiol., 10:170, Feb. 7, 2019.

* cited by examiner

*Primary Examiner* — Robert B Mondesi
*Assistant Examiner* — Mohammad Y Meah
(74) *Attorney, Agent, or Firm* — US Naval Research Laboratory; Roy Roberts

(57) ABSTRACT

"Biocathode MCL," designated for its main bacterial constituents (*Marinobacter*, Chromatiaceae, and *Labrenzia*), is a stable microbial community enriched from seawater that forms biofilms on the surfaces of electrodes. These biofilms are effective to perform carbon fixation without the need for external electrical power nor sunlight applied thereto.

4 Claims, 6 Drawing Sheets

| Condition | Cell count | Cells/6.25 cm² | Cell viability |
|---|---|---|---|
| Experiment 1 | | | |
| ITO/Ti-OCP | 300 | 1.2 X 10⁶ | 59% |
| Glass | 300 | 4.7 X 10⁵ | 41% |
| ITO/Ti-OCP | 30 | 9.5 X 10⁵ | 66% |
| Glass | 30 | 1.7 X 10⁵ | 89% |
| ITO/Ti-set pot. | 300 | 1.3 X 10⁷ | 69% |
| Experiment 2 | | | |
| ITO | 1100 | 3.9 X 10⁶ | 68% |
| Glass | 1100 | 1.3 X 10⁵ | 99% |
| ITO/Ti-OCP | 110 | 6.2 X 10⁵ | 77% |
| Glass | 110 | 1.7 X 10⁵ | 99% |
| ITO/Ti-set pot. | 110 | 2.7 X 10⁵ | 87% |
| Experiment 3 | | | |
| ITO/Ti-OCP | 700 | 2.0 X 10⁵ | 100% |
| Glass | 700 | 1.4 X 10⁵ | 90% |
| ITO/Ti-set pot. | 700 | 2.7 X 10⁷ | 89% |
FIG. 4A
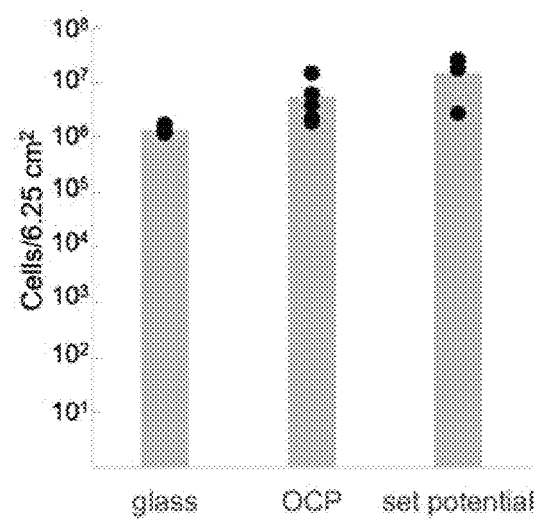
FIG. 4B
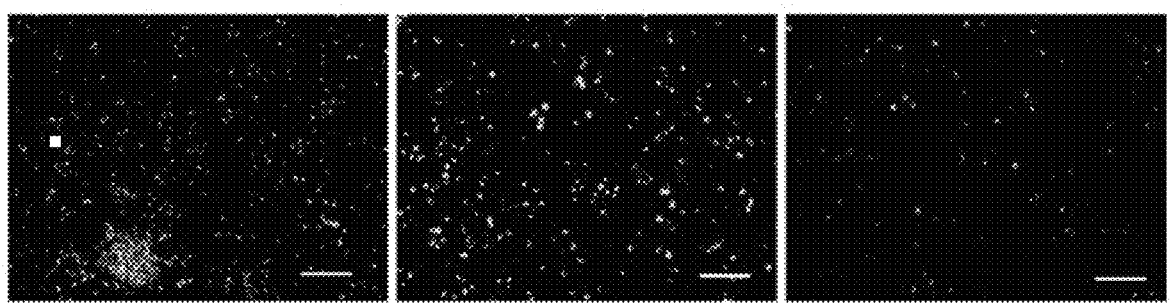
FIG. 4C

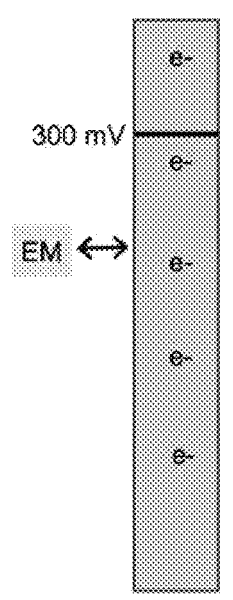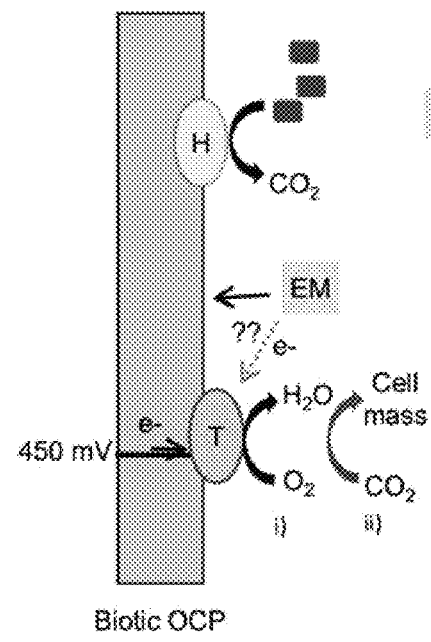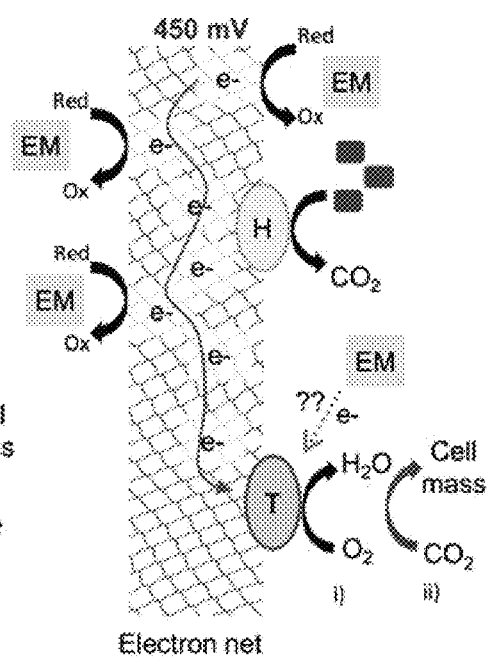
Abiotic OCP
FIG. 6A
Biotic OCP
FIG. 6B
Electron net
FIG. 6C

CONDUCTIVE MATERIALS TO DRIVE BACTERIAL CARBON DIOXIDE FIXATION

CROSS-REFERENCE TO RELATED APPLICATIONS

This application claims the benefit of U.S. Provisional Patent Application No. 62/947,327 filed on Dec. 12, 2019, incorporated herein by reference in the entirety.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 111,475.

BACKGROUND

The metabolic processes required for bacterial growth and maintenance involve acquiring relatively high energy electrons and giving up relatively low energy electrons. Metal-oxidizing bacteria can use metals, minerals, metal surfaces, mineral surfaces, or electrode surfaces (and combinations of these) which are poised at sufficiently reducing potentials as extracellular electron donors for carbon fixation through extracellular electron transfer (EET) processes that facilitate electron transfer from an extracellular electron donor to anabolic processes occurring inside a bacterial cell. In contrast, metal-reducing bacteria use metals, minerals, metal surfaces, mineral surfaces, or electrode surfaces (and combinations of these) which are poised at sufficiently oxidizing potentials as extracellular electron acceptors that reside outside the cell body through EET processes that facilitate electron transfer from catabolic processes occurring inside a bacterial cell to an extracellular electron acceptor.

Those bacteria that employ insoluble extracellular electron donors for carbon fixation from seawater typically use electron donors that take the form of insoluble minerals, such as iron that can be depleted over time.

Bacteria in the environment live in microbial communities, forming biofilms comprised of bacterial cells and extracellular substances comprised of proteins, biopolymers and other secreted cellular materials that adhere to surfaces. Biofilms help to establish stable growth conditions for bacteria and to protect against exposure to any number of environmental insults, including changes in salinity, pH, and chemical exposure. "Biocathode MCL"[10], designated for its main bacterial constituents (*Marinobacter*, Chromatiaceae, and *Labrenzia*), is a stable microbial community enriched from seawater that forms biofilms on the surfaces of electrodes. Of the roughly 16-20 different bacterial constituents comprising the Biocathode MCL community, "Ca. *Tenderia electrophaga*" a member of the Chromatiaceae, utilizes electrode surfaces poised at sufficiently reducing potentials as extracellular electron donors for carbon fixation through EET processes. This capability, termed "electroautotrophy" has significant technological implications in that it enables coupling of renewal sources of electrical power to drive electrochemical conversion of carbon dioxide to fuel precursors (i.e., carbon capture) as part of closed carbon cycle in which a bacterial biofilm acts as a self-assembling and self-maintaining electrode catalyst and for which conventional (abiotic) electrode catalysts do not exist. "Ca. *Tenderia electrophaga*" performs electroautotrophy by using electrons obtained from the electrode to reduce oxygen and nicotinamide adenine dinucleotide (NAD+) to generate reducing equivalents for carbon fixation.

Recent work with Biocathode MCL involved growth at electrodes poised at a sufficiently reducing potential as electrons donors for bacterial carbon fixation which requires continuous application of electrical power.[15] A need exists for improved techniques to implement carbon fixation by such bacterial biofilms.

BRIEF SUMMARY

In one embodiment, the surface of an unpoised electrode (i.e., an electrode at open circuit) immersed in a medium (i.e., water with or without added substances) is an effective electron donor for bacterial carbon fixation without the need for external electrical power applied to the electrode, whereby an attached biofilm utilizes the surface of an electrode at open circuit as an electron donor that provides a finite supply electrons to the bacteria.

In another embodiment, the surface of an unpoised electrode (i.e., an electrode at open circuit) immersed in a medium is an effective electron donor for bacterial carbon fixation without the need for external electrical power applied to the electrode, whereby an attached biofilm utilizes the surface of an electrode at open circuit as an electron donor that provides a finite supply electrons to the bacteria. The resulting ennoblement in turn enables the bacteria to access an additional unlimited supply of electrons from oxidation by the electrode of mineral electron donors present in the medium that would otherwise be inaccessible the bacteria.

In a further embodiment, an apparatus for studying electroautotrophy includes a reactor vessel containing natural or artificial seawater; an unpoised working electrode immersed in the seawater; a reference electrode immersed in the seawater; a counter electrode immersed in the seawater; and an electroautotrophic biofilm living attached to the working electrode.

BRIEF DESCRIPTION OF THE DRAWINGS

FIG. 2A provides results of an abiotic reactor held at 0.490 V SHE for 18 days. FIG. 2B shows the open circuit potential (OCP) of an abiotic reactor after being held at 0.290 V for 18 days.

FIG. 2C presents data from reactors held at 0.490 V SHE with and without trace mineral solution added to the electrochemical reactors containing the electrodes. No difference between the two conditions was observed. Trace minerals were added to individual reactors so that the basal medium was identical.

FIG. 3A shows the effect of ampicillin, kanamycin (added) at day 12 after inoculation with Biocathode MCL), and cyanide (added at day 18 after inoculation with Biocathode MCL) on the potential shift at OCP. FIG. 3B shows the effect of antibiotics added at day 26-28 after inoculation with Biocathode MCL.

FIGS. 4A and 4B show the cell counts (i.e., the number or cells) comprising Biocathode MCL biofilms that grew on indium tin oxide (ITO) electrodes. ITO electrodes at open circuit consistently had higher cell counts than glass slide controls across three independent experiments and four different concentrations of cells added initially whereby glass controls do not act as bacterial electron donors. FIG. 4C provides representative images of cells on a 0.310V SHE set potential electrode (left), open circuit electrode (middle), and glass slide (right) using Live/Dead stain. Scale bar=20 μm.

FIGS. 6A-6C illustrate a proposed model of utilization of an electrode at open circuit as an electron donor by Biocathode MCL based on results depicted in FIGS. 1-5. In FIG. 6A, the abiotic OCP is determined by interaction with the electrode with an electroactive molecule or molecules in the medium (depicted as EM). FIG. 6B shows that, after inoculation with Biocathode MCL, the electroautotrophic member of the community "*Candidatus Tenderia electrophaga*" (T) acquires electrons associated with the electrode double-layer capacitance for (i) oxygen reduction to provide energy and (ii) carbon fixation to generate reduced carbon, leading to a more positive OCP. At the same time, heterotrophic members (H) of the Biocathode MCL community, which are not able to fix carbon themselves, may incorporate reduced carbon compounds contained in the medium (red squares). In addition heterotrophic members (H) of the Biocathode MCL community may incorporate reduced carbon compounds generated by "Ca. *Tenderia electrophaga*" (T). In addition, "Ca. *Tenderia electrophaga*" (T) may also use EM directly as an electron donor. FIG. 6C illustrates that, as the OCP becomes more positive, it acts as an electron net, increasing the cell's effective electron accepting surface area by accepting electrons from the EM as they are transformed from the reduced (Red) to oxidized state (Ox) by the electrode.

DETAILED DESCRIPTION

Definitions

Figure 1A:
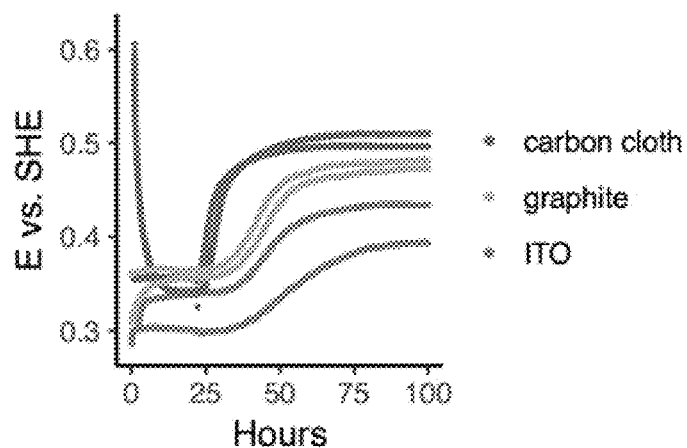
FIG. 1A shows that the open circuit potentials (OCP) became more positive for graphite, carbon cloth, and indium tin oxide (ITO) coated glass electrodes on which Biocathode MCL biofilms were grown.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, the term "carbon fixation" refers to the chemical reduction of carbon dioxide to one or more organic compounds, such as those employed by bacterial cells for growth and maintenance.

Overview

Energy for carbon fixation can also be derived from electrons distributed to attached biofilms through conductive materials. The "electron net" is a process by which electrons are captured by a conductive material, e.g. a carbon cloth electrode, via oxidation of electron donors in seawater due to the electrode potential and continuously transmitted to bacteria attached to conductive material to provide electrons for carbon fixation.

Given the recent discovery of "Ca. *Tenderia electrophaga*" in other microbial biofilm communities living on corroding stainless steel surfaces in marine settings that undergo a positive shift in open circuit potential (OCP), a process termed "ennoblement," it was found that Biocathode MCL gains a metabolic benefit from a non-corrosive conductive electrode material at open circuit. Here, the capacitive charge of the electrode is a finite source of electrons which does not require application of external electrical power resulting in ennoblement of the electrode whereby a positive shift in OCP reflects that the electrode at open circuit is acting as an electron donor. Moreover, if the ennoblement shifts the OCP sufficiently positive such that the electrode can oxidize electron donors such a minerals present in the medium or seawater, then the electrode can serve to mediate electron transfer from such donors to the bacterial cells to indefinitely sustain electroautotrophy without the application of electrical power.

As described herein, the electrode OCP became positive as the Biocathode MCL biofilm formed on graphite, carbon cloth, or indium tin oxide (ITO) electrodes, reaching a maximum OCP near the midpoint potential of Biocathode MCL. Here, midpoint potential refers to the potential applied to an electrode at which the rate of electron uptake by an attached Biocathode MCL biofilm is half its maximum value, and is taken to reflect the upper limit of potential of electrons that "Ca. *Tenderia electrophaga*" of Biocathode MCL can utilize for oxygen reduction and carbon fixation. Concurrent with the positive shift in open circuit potential (ennoblement), an increase in the number of cells on ITO electrodes was observed relative to glass slides, as well as an increase in the proportion of "Ca. *Tenderia electrophaga*", demonstrating that electroautotrophic bacteria can utilize electrons associated with the electrode double-layer capacitance for carbon fixation. Maintaining the ennoblement required living cells, demonstrated by addition of antibiotics. An abiotic electrode held at the potential reached by the ennoblement produced current, indicating the presence of electrode reactive molecules in the medium. As Biocathode MCL forms sparse biofilms in which most of the electrode surface remains uncolonized by cells, it is proposed that the ennobled electrode acts as an "electron net" by capturing a larger flux of electrons from electrons donors compared to cells alone. The ability of a biofilm to directly cause and maintain the ennoblement of non-corrosive electrodes by scavenging electrons from electroactive molecules is significant because it suggests that conductive materials in the environment could collect charge from trace elements at a distance from the physical location of cells. This phenomenon may explain the persistence of metal-oxidizing bacteria in the environment under nutrient-limiting conditions, as well as persistent ennoblement leading to microbially influenced corrosion Significantly, seawater can serve as a continuous source of electrons by providing an electrode with a fixed applied potential that mimics mineral electron donors but in practice cannot be depleted.

EXAMPLES

Materials and Methods

Biocathode MCL was cultivated in artificial seawater (ASW) medium containing 27.50 g NaCl, 3.80 g $MgCl_2 \cdot 6H_2O$, 6.78 g $MgSO_4 \cdot H_2O$, 0.72 g KCl, 0.62 g $NaHCO_3$, 5.58 g $CaCl_2 \cdot H_2O$, 1.00 g $NH_4Cl$, 0.05 g $K_2HPO_4$, and 1 ml Wolfe's Trace Mineral Solution per liter. The $NaHCO_3$ was autoclaved in a separate sealed bottle and added after cooling to avoid precipitation. The medium was adjusted to a pH between 6.5 and 6.8 by briefly bubbling with 100% $CO_2$. Source cultures were continuously maintained in 2 liter, 3-electrode reactors with carbon cloth as working and counter electrodes. The working electrode was poised at 0.310 V SHE (standard hydrogen electrode).

For these experiments, bioelectrochemical systems (BES) were 175 ml glass electrochemical reactors (Pine Instruments, Grove City, Pa.). Working electrodes were either 10.5 $cm^2$ graphite flags (Tri-Gemini, Hillside, Ill.) or carbon cloth (Fuel Cell Earth, Woburn, Mass.) cut to roughly 3.5×1.5 cm for an area of 10.5 $cm^2$. Counter electrodes were carbon cloth electrodes cut to approximately 3.5×1.5 cm. Graphite flags were sanded down prior to cleaning. Both carbon cloth and graphite flag electrodes were soaked overnight in 1 M hydrochloric acid, then rinsed and soaked overnight in ultrapure deionized water (MilliQ, Millipore-Sigma, Burlington, Mass.). Electrodes were suspended in the reactors from titanium wires, attached by titanium screws. The reference electrodes for the experiments were 3 M KCl Ag/AgCl (BASI, West Lafayette, Ind.) washed in bleach and rinsed in sterile ultrapure deionized water. All potentials are reported here as vs. SHE by adding 0.21V to the experimental potentials vs. Ag/AgCl.

For reactors used for microscopy, glass reactors were washed with 10 N sodium hydroxide dissolved in 60% isopropanol to remove residual organic carbon and rinsed in ultrapure deionized water. Working electrodes were 6.46 $cm^2$ glass slides coated on one side with ITO (Sigma, St. Louis, Mo., USA). The slides were attached to titanium wires by clamping between two titanium washers, washed in concentrated sulfuric acid, rinsed in ultrapure deionized water, then washed in bleach and rinsed in sterile ultrapure deionized water. Counter electrodes were platinum mesh attached to titanium wires, washed in concentrated sulfuric acid, rinsed in ultrapure deionized water, and autoclaved in ultrapure deionized water in the reactors. For controls, glass slides were used in place of the ITO electrodes, suspended from titanium wires and washed in the same way as the working electrodes, with the titanium held above the surface of the medium to avoid the presence of a capacitive surface in the reactor.

Once assembled, the BES were maintained at 30° C. using water jackets and stirred using small stir bars and stir plates (VWR, Radnor, Pa., USA). The electrodes were connected to a multichannel potentiostat (Biologic, Seyssinet-Pariset, France), which was used to record cyclic voltammograms at fast (20 mV/S) and slow (0.2 mV/S) scan rates, and then to monitor the OCP or, for experiments with set potential, to hold the potential at 0.310 V and monitor current production. After the signal stabilized, the reactors were inoculated with 1 ml of initial inoculum diluted $10^{-3}$ or $10^{-4}$-fold. Based on the cell counts of filtered inoculum, reactors in experiment 1 were inoculated with ca. 30 or ca. 300 cells, while reactors in experiment 2 were inoculated with ca. 110 or ca. 1100 cells and reactors in experiment 3 were inoculated with 700 cells.

The quantity of electrons extracted by MCL from an open circuit electrode was taken as the product of the electrode double-layer capacitance and the change in OCP. Cyclic voltammetry was performed on each working electrode type at 0.02 V/s in the ASW medium before inoculation. Double-layer capacitance ($C_d$) was determined for each electrode type by application of the law of capacitance ($C_d$=i/v), where i is current and v is voltammetric scan rate, noting that i=dq/dt where q is charge attributed to electrochemically accessible electrons on the electrode surface and v=dE/dt where E is the electrode potential and t is time[18]. The moles of electrons extracted from an open circuit electrode accompanying a change in OCP follows as $\Delta(mole\ e^+)=\Delta q/F$ where $\Delta q=C_d \Delta E$ (law of capacitance), $\Delta q$ is the change in charge, $\Delta E$ is the change in OCP, and F is the Faraday constant. Cyclic voltammetry performed after the OCP changed indicated that $C_d$ was unaffected by the sparse biofilms that grew on the electrodes. As indicated by the calculations, if electrons associated with the double-layer capacitance of an open circuit electrode are the only source of electrons, then no electrons can be extracted without a positive shift in the OCP.

The maximum amount of energy that can be obtained by MCL acquiring electrons from an open circuit electrode ($U_{oc}$) was determined by integrating over time the product of the quantity of electrons extracted and the difference in energy of the electrons entering cells from the electrode (indicated by the instantaneous OCP) and leaving the cells through $O_2$ reduction (case for Biocathode MCL). Given the linear relationship between the change in charge and change in OCP ($\Delta q=C_d \Delta E$), it follows that $U_{oc}=C_d \Delta E(OCP_{Avg}-0.81)$ where $OCP_{avg}$ is the average of the OCP recorded before inoculation and after the OCP had shifted and leveled off following inoculation, and 0.81 V is the formal potential of $O_2$ reduction at the conditions in the reactors. As this calculation indicates, once a shift has occurred and OCP levels off, no additional energy is obtained if electrons associated with the electrode double-layer are the only source of electrons.

For comparison, the maximum amount of energy acquired by Biocathode MCL grown on an electrode maintained at 0.310 V ($U_{310}$) was determined by integrating over time the product of the quantity of electrons extracted and the difference in energy of the electrons entering cells from the electrode (0.310 V) and leaving the cells through $O_2$ reduction. It follows as above that $U_{310}=\Sigma dU_{310}$ where $dU_{310}=dq \times (0.310-0.81\ V)$ and $dq=i_{avg} \times dt$, where $i_{avg}$ is the average of current measured at the beginning and end of each time increment of dt (25 s). These calculations indicate that 35 µmoles $e^-$ yielding 172 mJ of energy was obtained in 110 hrs of growth.

ITO working electrodes were removed from the reactors and broken into ~0.5-1 cm pieces. Two of the pieces were immediately stained with BacLight live-dead stain (ThermoFisher, Waltham, Mass., USA), and the rest were fixed for fluorescence in situ hybridization (FISH) using the protocol below. To obtain cell counts of the inoculum prior to inoculation of test reactors, 0.1 ml of the inoculum was filtered through a 0.2 μm black polycarbonate filter (Millipore, Burlington, Mass., USA). Confocal images of cells on filters or electrodes were taken with a Zeiss AxioObserver.Z1/7 LSM800 Airyscan confocal microscope using a Plan-Apochromat 40x/1.3 DIC (UV) VIS-IR M27 objective. For live/dead labeled cells, Syto9 and propidium iodide (PI) fluorescence spectra were excited at 488 nm: 0.20% laser power and 561 nm: 0.20% laser power, respectively. The emission spectra of Syto9 were collected with 490-550 nm filters and detected with the LSM 800 Airyscan detector. PI emission spectra were collected with 550-700 nm filters and detected with the LSM 800 GaAsP-Pmt2 detector. Each image was taken with a 2.09 μs pixel dwell, 10.13 s scan time per frame with 4× averaging. Images are maximum intensity projections composed of optical sections over a 10-15 μm Z-stack interval in a 160.66 μm×160.66 μm field of view. Cell counts were measured by the Zeiss Zen Image Analysis software. Cell boundaries were defined with automated segmentation based on cell size (between 0.25 um and 10 um) after Lowpass smoothing (3) and unsharp masking (5.0) to enhance local contrast. 8 images were taken across the two stained electrode pieces and averaged. Cell counts for the 6.25 cm$^2$ electrode were calculated by multiplying the average cell count by the electrode area divided by the image area.

FISH-labelled cells were imaged as above, with the following modifications: 4',6-diamidino-2-phenylindole (DAPI), Tel428-Tidefluor 2[10], and Gamma42a2-Tidefluor 3[19] (Eurofins, Louisville, Ky., listed in Table 2S) fluorescence spectra were excited at 405 nm, 506 nm, and 548 nm, respectively, all at 0.20% laser power. The corresponding emission spectra of each were collected using 400-489 nm (DAPI), 500-540 nm (Tel428-Tidefluor 2), and 583-700 nm (Gamma42a2-Tidefluor 3). The filtered emission spectra were detected using the GaAsP-Pmt1 (DAPI), Airyscan (Tel428-Tidefluor 2), and GaAsP-Pmt2 (Gamma42a2-Tidefluor 3) detectors. Images were collected and processed using the Zeiss Zen Blue imaging software (Carl Zeiss, LLC, Thornwood, N.Y., USA).

FISH probing was done using a modified version of the procedure previously described for Biocathode MCL[10]. Electrode fragments were fixed by incubation in 2% paraformaldehyde in ASW medium for 1 hour on ice. The samples were then coated with a solution of 1× nuclease-free PBS buffer (Ambion, ThermoFisher) with 0.1% low melt agarose and 0.1% paraformaldehyde and placed at 4° C. with desiccant overnight. Remaining moisture was driven off at 37° C., and dehydration was completed with 1-minute washes of 25% and 50% cold ethanol with 10 mM EDTA, followed by 75%, 90% and 100% cold ethanol. Samples were briefly placed in a desiccator, then stored in microcentrifuge tubes at 4° C. until staining.

Staining was performed by permeabilizing samples with 1 mg/ml lysozyme and 50 μg/ml protease K in PBS for 10 minutes at 37° C., rinsing in PBS, then incubating in FISH hybridization buffer (containing 29.2% NaCl, 10 mM EDTA (RNAse free, Ambion), 20 mM TRIS (RNAse free, Ambion), 30% formamide, and 0.025% triton X) with 500 nM FISH probes for 2 hours at 42° C., rinsing once with cold PBS, incubating in hybridization buffer with DAPI for 30 minutes at 42° C., and rinsing once with water. Prepared samples were embedded in ProLong Diamond (Life Technologies, Carlsbad, Calif., USA) on a chambered cover glass and stored at room temperature overnight before imaging.

Results

Figure 1B:
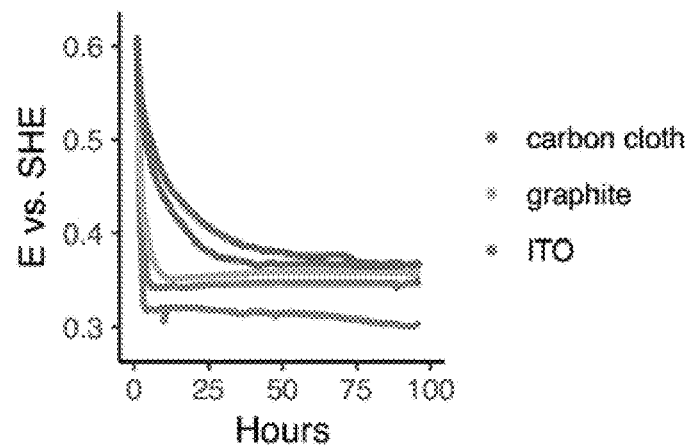
FIG. 1B shows that under abiotic conditions (i.e., sterile conditions when no bacterial cells are present), the OCP remained stable, between 0.3 and 0.4 V vs. a standard hydrogen electrode (SHE) for at least 100 hours.
Figure 1C:
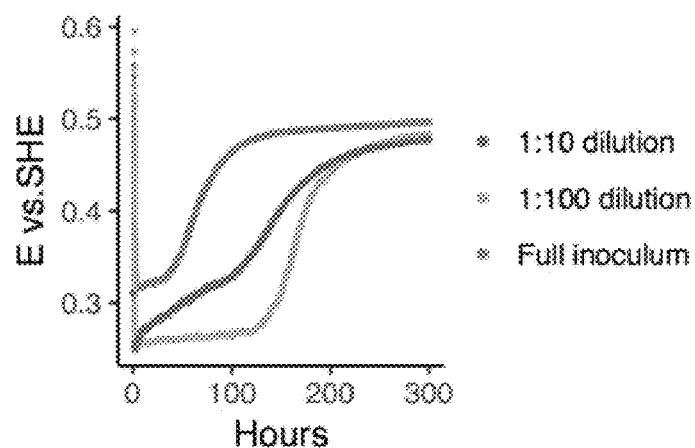
FIG. 1C shows that the amount of time required before the shift in OCP occurs, termed "lag time", that is induced by Biocathode MCL, increased with serial dilutions of the inoculum whereby the concentration of bacterial cells comprising Biocathode MCL in the inoculum initially added to electrochemical reactors containing the electrodes was increased.

It was previously proposed that Biocathode MCL is able to grow and catalyze electron transfer from electrodes poised at 0.310 V and $O_2$ and fix $CO_2$ via reverse electron transport through the activity of the putative electroautotroph "Ca. Tenderia electrophaga." Electron transfer is thought to occur by direct electron transport through redox cofactors associated with the cell membrane of "Ca. Tenderia electrophaga" driven by a more reducing potential at the electrode surface towards the higher potential electron acceptor, $O_2$, inside the cell. In order to determine whether Biocathode MCL can induce ennoblement by the spontaneous flow of electrons through this proposed electron transport pathway, BES were tested with either ITO, carbon cloth, or graphite electrodes at OCP and inoculated them with a portion of a biofilm from an electrode of a source reactor held at 0.310 V. Following inoculation, the OCP of the working electrode increased by 0.10-0.15 V from the abiotic OCP to a maximum potential of 0.35-0.5 V (exemplary data shown in FIG. 1A). The lag time before the increase was dependent on the dilution factor of the inoculum (FIG. 1B), but the final potential reached was similar whenever sufficient inoculum was used.

In order to determine whether the energy available from an open circuit electrode was sufficient to support bacterial growth, a calculation was made to ascertain how many electrons would need to be removed from the electrode to induce the observed positive shift in OCP based on the double-layer capacitance for each electrode material. The observed OCP shift correlated to the uptake of ca. 0.26 nmol of electrons from ITO electrodes, ca. 4.1 nmol of electrons from carbon cloth, and ca. 21 nmol of electrons from graphite electrodes. The maximum theoretical energy available from the transfer of electrons from the electrode to oxygen was 12 μJ for ITO electrodes, 150 μJ for carbon cloth electrodes, and 750 μJ for graphite electrodes. In contrast, when Biocathode MCL was grown on a graphite electrode held at 0.310 V for 110 hrs, it drew ca. 35 μmol of electrons. This corresponds to 172 mJ, determined by the product of the quantity of electrons (35 μmop and the difference in potential energy of electrons between leaving the electrode and being taken up by oxygen (0.310 V−0.810 V=−0.5 V), which is orders of magnitude greater than the energy conserved from any of the open circuit electrodes.

To estimate the cell yield that might be expected from OCP electrodes, the yields reported for microaerobic iron-oxidizing autotrophs were used. Neubauer et al.[20] concluded that 1 mole of Fe(II), when oxidized, yielded $2.9 \times 10^4$ Joules (when linked to oxygen reduction) and supported the growth of ca. $5 \times 10^{13}$ cells. Based on the energy available from each electrode type, the capacitive charge (assuming the same conversion rates as found for iron-oxidizers) yields on graphite would be $1.5 \times 10^6$ cells (from 750 μJ), while the yields on ITO would be $3 \times 10^5$ cells (from 150 μJ), or $2.4 \times 10^4$ cells (from 12 μJ).

Figure 2A:
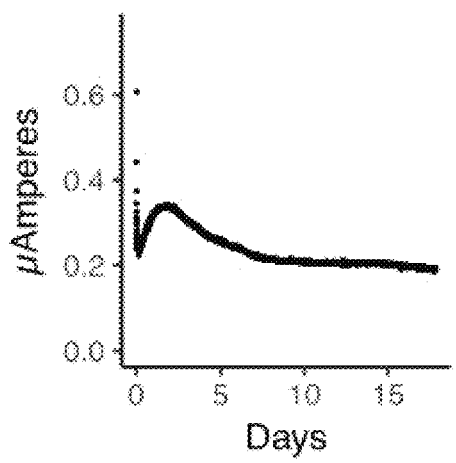
FIGS. 2A-2C shows abiotic current production of electrodes poised at 0.490 V vs SHE.
Figure 2B:
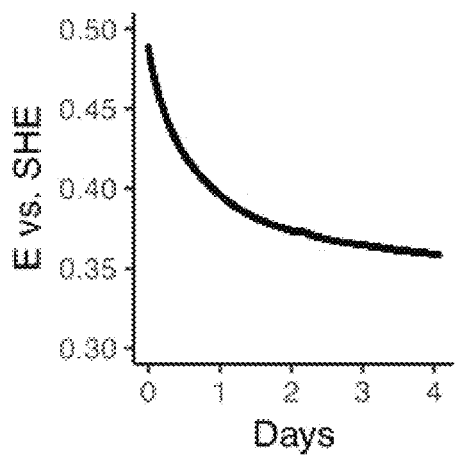
Figure 3A:
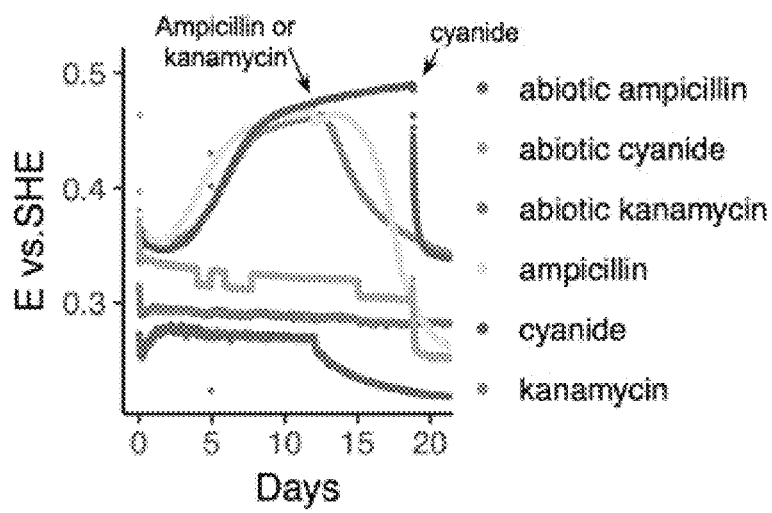
FIGS. 3A and 3B illustrate the effect of the addition of antibiotics on the open circuit potential (OCP).
Figure 3B:
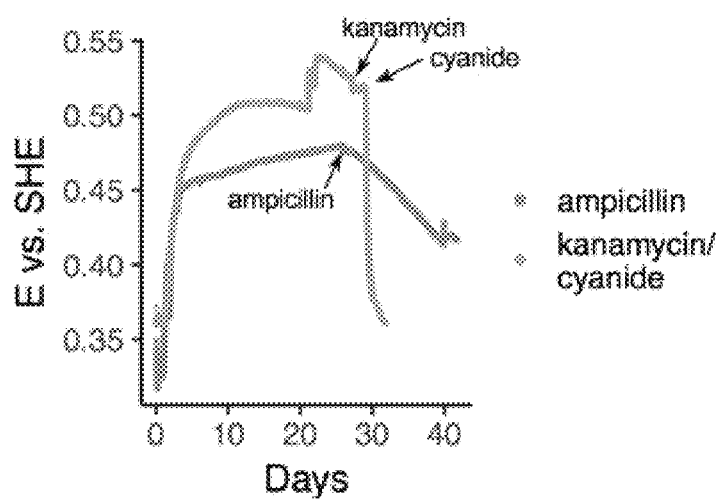

The possibility of abiotic current production from an unknown electron donor in the medium was examined. The calculations for capacitive charge described above make the assumption that once the OCP has stabilized, no further electrons are available to Biocathode MCL. To confirm this assumption, chronoamperometry was performed on an abiotic reactor with a graphite electrode poised at the same potential as the maximum OCP observed in inoculated reactors (0.490 V). Contrary to prediction, the abiotic reactor produced 200 nA of current for 18 days (FIG. 2A). After 18 days, the abiotic reactor was placed at open circuit, and the OCP decreased over ca. 72 hours back to its original value (FIG. 3B). The amount of current produced was variable over different experiments: The experiment shown in FIG. 2A stabilized at 200 nA, while reactors shown in FIG. 2B stabilized at 1-2 µA. A reactor tested with an ITO electrode produced 5 nA. Nonetheless, all abiotic reactors investigated produced anodic current when poised at 0.490 V.

The current in the abiotic reactor shown in FIG. 2A was integrated over time, and indicated that 6 µmol electrons were taken up by the electrode over 18 days, suggesting that electroactive molecules are present in the reactor. It was hypothesized that the additional electrons may originate from the trace minerals added to the medium. To test this, abiotic reactors were operated with and without added trace minerals. The reactors without trace minerals produced similar amounts of background current to those with trace minerals (FIG. 2B). Though the electroactive molecules in the medium could not be positively identified, they presumable arose from the salts, water, and/or other trace contamination.

Figure 2C:
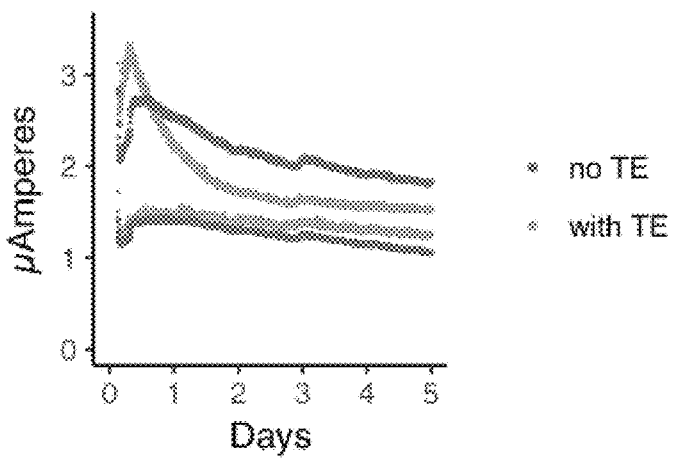

The effect of antibiotics on the open circuit potential was examined in order to determine whether the maintenance of the OCP was dependent on metabolically active cells. Because ampicillin kills only dividing cells (by interfering with cell wall formation[21]), while kanamycin kills by interfering with translation machinery (killing bacteria that are actively manufacturing proteins[21]), these antibiotics were used to determine the rough metabolic state of the cells. Current production is inhibited by both kanamycin at 25 µg/ml and ampicillin at 100 µg/ml when the electrode potential is set at 0.310 V, indicating that the community is sensitive to both of these antibiotics. As shown in shown in FIG. 2, addition of kanamycin 10 days after inoculation resulted in a drop in OCP that began within a day (13 hours in one experiment, 10 hours in another) and ended at an OCP below the pre-inoculation OCP. Ampicillin also caused the OCP to return to its pre-inoculation level; however, the decrease in potential was delayed, taking 2-3 days to begin dropping.

To test how long the cells remained active and sensitive to antibiotics, reactors were incubated for 26 days before antibiotic additions. The inoculated reactors maintained an OCP close to 0.50 V vs. SHE during the 26-day incubation. Kanamycin, added 27 days after inoculation (FIG. 3B), did not cause a decrease in OCP after 2 days (longer times were not tested). Ampicillin, added 26 days after inoculation (FIG. 3B), showed OCP reduction beginning at two days, but the drop was extremely slow, not returning to the abiotic OCP even after two weeks. Cyanide, which inhibits cytochrome function, caused an immediate drop in potential in both old and young reactors (FIGS. 3A and 3B).

Figure 5:
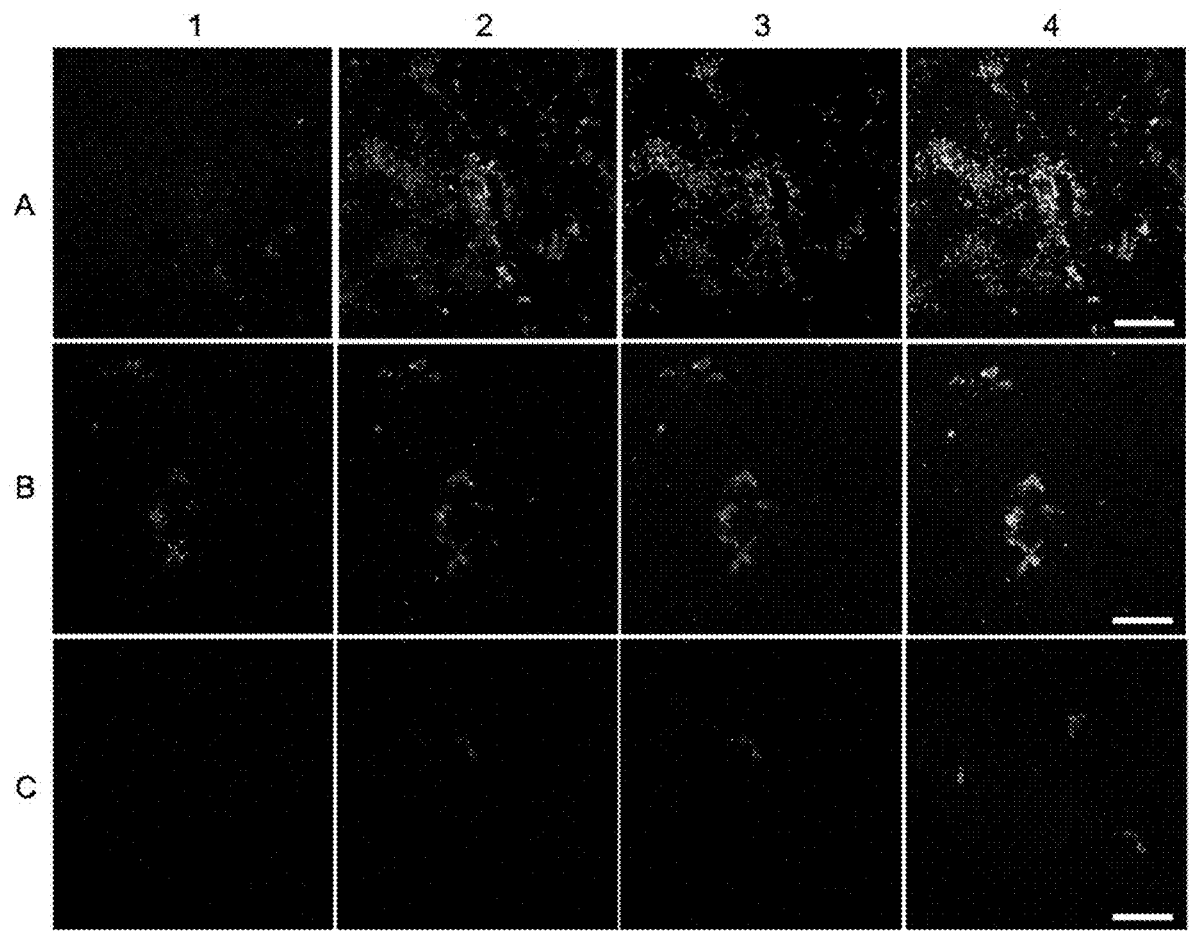
FIG. 5 shows fluorescence in situ hybridization (FISH) of biofilms at 0.310V SHE set potential (A), Open circuit indium tin oxide (ITO) (B), and glass slide (C), stained with 4',6-diamidino-2-phenylindole (DAPI) (1), a "*Candidatus Tenderia electrophaga*" binding probe (2), a Gammaproteobacteria binding probe (3), and an overlay of all three stains (4). Scale bar=20 μM

Although reactors with glass slides had increased cell numbers, there was a significant difference between the ITO and plain glass slide reactors consistent across all experiments; the ITO slides showed increased cell numbers over the glass slides where glass slide are unable to act as electron donors (FIG. 4). This trend held up across three independent experiments, with two of the experiments starting out with two initial dilutions and the third experiment with one dilution. Additionally, the electrode surfaces showed a higher proportion of "Ca. Tenderia electrophaga" than the glass slides by FISH probing (FIG. 5), consistent with electroautotrophic ennoblement. The final number of cells did not depend on the initial dilution, suggesting that the inoculum was not the source of growth substrate.

Discussion

When added to an electrochemical reactor containing an unpoised non-corroding graphite, carbon cloth, or ITO electrode, Biocathode MCL was able to induce ennoblement. Concurrent with the ennoblement, an increase in the number of cells on the electrodes was observed relative to glass slides in control reactors, as well as an increase in the proportion of "Ca. Tenderia electrophaga", indicating cell growth. The increase in cell mass under these conditions denotes carbon fixation, with $CO_2$ as a carbon source. Maintaining the electrode ennoblement (the more positive potential), which persisted over weeks, required that the cells remain viable, as demonstrated by addition of antibiotics. Taken together, these results suggest that Biocathode MCL can employ the following metabolic strategy, depicted in FIG. 6, termed now an "electron net": "Ca. Tenderia electrophaga" takes up electrons stored as capacitive charge from the surface of an electrode at open circuit, causing the electrode OCP to become more positive. The positive shift in OCP makes the electrode a viable mediator for electron transfer from a yet to be identified electroactive molecule in the medium, demonstrated by anodic current observed from abiotic electrodes poised at 0.490 V. The unidentified electroactive molecule is oxidized by the electrode and the liberated electrons are taken up from the electrode by "Ca. Tenderia electrophaga" at the same rate (i.e., there is no net change in number of electrons residing on the electrode surface). Key to this strategy is the large surface area of the mostly uncolonized electrode, which can capture a larger flux of the trace electroactive molecule compared to a single cell, and the electroautotrophic ability of "Ca. Tenderia electrophaga", which can take up electrons directly from the electrode. When trace minerals are omitted from the medium, abiotic current is still observed, suggesting that the redox species is either one of the salts in the medium or a trace metal contaminant in one of the salts. In addition to expanding the understanding of how electroautotrophic bacteria such as "Ca. Tenderia electrophaga" may live in marine environments, the strategy described here has significant technological implications in that electroautotrophic bacteria may be able generate reduced carbon compounds for a multitude of applications including precursors for fuels (i.e., carbon capture) as part of closed carbon cycle in which a bacterial biofilm acts as a self-assembling and self-maintaining electrode catalyst and for which conventional (abiotic) electrode catalysts do not exist, whereby, due to ennoblement of the conductive material by the biofilm, the cells can draw unlimited amounts of electrons from oxidation of mineral electron donors present in seawater without added electrical power.

The maximum OCP observed in the reactors was ca. 0.49 V, which agrees well with the midpoint potential previously determined for Biocathode MCL[15] and suggests that the ennoblement is a result of direct bacterial activity. However, although a final OCP higher than 0.49 V was not seen, there was considerable variability both in the initial OCP of the abiotic electrodes and the final OCP reached. In reactors that did not reach 0.49 V, the rate that electrons were taken up by Biocathode MCL may balance the rate at which the electrode can acquire electrons from trace donors at a lower potential.

The increase in OCP has a lag time that depends on the dilution of the initial inoculum. This may reflect time required for "Ca. Tenderia electrophaga" to form the syntrophies it needs with the other organisms in Biocathode MCL, or might reflect an initial period of growth in which the electrons drawn by so few cells do not produce a large enough signal to be distinguished even by OCP shifts. This possibility is complicated by the presence of the proposed unknown electron donor: the donor might be able to donate electrons to the electrode, or even to the cells directly, to keep the OCP at its initial level. Once the positive shift in OCP begins, however, its rate of increase appears to be exponential and not dependent upon the initial cell numbers, suggesting that cells are dividing during this time.

The higher cell counts and higher proportion of "Ca. Tenderia electrophaga" on electrodes versus glass demonstrates that the electrode is available as an electron donor and ennoblement of the electrode results in Biocathode MCL growth. Glass slide controls, which cannot act as electron donors, showed that cell growth still occurred in the absence of a conductive material, but that a higher proportion of heterotrophs to "Ca. Tenderia electrophaga" were present on the glass compared to electrodes. The growth of heterotrophic organisms suggests that trace organic carbon is accessible to at least some of the cells directly.

The decrease in OCP with the addition of either ampicillin or kanamycin 10 days after inoculation strongly suggests that the increase in OCP is due to activity of living cells rather than enzymatic activity alone, as has been previously proposed to drive ennoblement under similar conditions.[22] The OCP response to antibiotics was slower and less pronounced 26-27 days after inoculation, suggesting that over longer time scales, cell division and protein production slow. The metabolism of "Ca. Tenderia electrophaga" in Biocathode MCL might reasonably be expected to become slower over an extended period of time due to the low electron flux at OCP: extrapolating from the abiotic experiments with a poised potential of 0.490 V, Biocathode MCL can obtain between ca. 200 pmol electrons/hr and ca. 80 nmol electrons/hr from the unknown electroactive molecule. In contrast, the Biocathode MCL on an electrode poised at 0.310 V harvested ca. 1.3 µmol electrons/hr, nearly 20× the electrons available from any of the OCP reactors. Despite its presumably reduced metabolism, the observation that the OCP immediately drops following addition of cyanide suggests that respiration is still actively occurring. This observation is important because it could suggest a key to how cells persist on surfaces in the marine environment when their metabolism is very slow, even if respiration is not.

Together, these results suggest a mechanism for a mixed community to survive and grow using a conductive surface to access electrons stored in the material as capacitive charge. The resulting ennoblement allows the surface to act as a mediator to access redox active elements in the surrounding environment once the potential becomes favorable as an electron acceptor. The possibility that conductive materials or minerals in the environment could serve as redox mediators for electrons either from syntrophic partners or from elements located in an inaccessible environment (e.g. hydrothermal vent) is not new[23,24]; however, to date the idea that microbial activity adjusts the potential of the conductive material to facilitate electron transfer has not been suggested and the OCP of such materials have not been monitored. Biocathode MCL contains heterotrophs that persist alongside "Ca. Tenderia electrophaga" even after years of sub-culture. One of these partners, *Marinobacter atlanticus* strain CP1, has been shown to use an electrode as an electron acceptor at 310 mV and 510 mV even when $O_2$ is present[25], suggesting that conductive materials can be used as electron acceptors by some organisms if the potential becomes such that it is thermodynamically favorable.

Cell counts reported here were made in base-washed glassware with acid washed electrodes, ultrapure water, and purified salts. Even under these conditions, both the electroautotroph "Ca. Tenderia electrophaga" and the heterotrophic members of Biocathode MCL were able to survive and grow using trace contaminants in the medium. This suggests the hypothesis that for a biofilm on a conductive surface in a marine (or other) environment with low concentrations of redox active molecules present, the mechanism proposed above could play a significant role in the survival and growth of metal-oxidizing organisms. The conductive material could behave as an electron net, capturing electrons from trace electroactive molecules far from where the cell is physically located, allowing cells to grow using substrates that are too dilute to be directly useful to single cells. Finally, the increase in OCP suggests a more direct bacterial-based mechanism for metal ennoblement in the environment where living cells sustain the more positive potential for survival rather than a purely enzymatic or chemical process with no metabolic benefit to the biofilm, consistent with the recent identification of Ca. Tenderia electrophaga as a biomarker of stainless steel corrosion[9].

Further Embodiments

It is expected that techniques described herein might find applications in the field in addition to being useful in the laboratory.

Carbon fixation can be employed as part of a bioremediation strategy. One or more organisms that comprise Biocathode MCL might be introduced on a suitable substrate (such as activated carbon) in order to promote bioremediation, for example the bioremediation of an aquatic sediment. The use of the substrate as an electron net allows the organisms to access even very dilute sources of electrons, suggesting that the technology might be useful in remediating extremely low concentrations of contaminants.

The ability of the system to capture carbon without added energy also has potential application. For example, one or more organisms that comprise Biocathode MCL might be introduced on a suitable substrate (such as activated carbon) to help clean a waste stream such as wastewater.

Advantages

This invention offers a method for harnessing the reducing power of chemicals in the ocean using an electrode to fuel carbon capture. Such a process as applied in previous designs required power input into the system to keep an applied potential at the electrode. In this design, an electrode or other conductive material is used at its open circuit voltage, without need for additional power (such as sunlight or an external source of electric power). It is possible that carbon captured in this way might help reduce quantities of this greenhouse gas.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Hall-Stoodley, L., Costerton, J. W. & Stoodley, P. Bacterial biofilms: From the natural environment to infectious diseases. *Nature Reviews Microbiology* 2, 95-108, doi: 10.1038/nrmicro821 (2004).
2. Hernandez, M. E. & Newman, D. K. Extracellular electron transfer. *Cell Mol Life Sci* 58, 1562-1571, doi:Doi 10.1007/P100000796 (2001).
3. Barco, R. A. et al. New Insight into Microbial Iron Oxidation as Revealed by the Proteomic Profile of an Obligate Iron-Oxidizing Chemolithoautotroph. *Appl Environ Microbiol* 81, 5927-5937, doi:10.1128/AEM.01374-15 (2015).
4. Bird, L. J., Bonnefoy, V. & Newman, D. K. Bioenergetic challenges of microbial iron metabolisms. *Trends Microbiol* 19, 330-340, doi:10.1016/j.tim.2011.05.001 (2011).
5. Byrne, J. M. et al. Redox cycling of Fe(II) and Fe(III) in magnetite by Fe-metabolizing bacteria. *Science* 347, 1473-1476, doi:10.1126/science.aaa4834 (2015).
6. Kato, S., Hashimoto, K. & Watanabe, K. Microbial interspecies electron transfer via electric currents through conductive minerals. *Proceedings of the National Academy of Sciences of the United States of America* 109, 10042-10046, doi:10.1073/pnas.1117592109 (2012).
7. Chen, S. S. et al. Promoting Interspecies Electron Transfer with Biochar. *Scientific Reports* 4, doi:ARTN 501910.1038/srep05019 (2014).
8. Chen, S. S. et al. Carbon cloth stimulates direct interspecies electron transfer in syntrophic co-cultures. *Bioresource Technology* 173, 82-86, doi:10.1016/j.biortech.2014.09.009 (2014).
9. Trigodet, F. et al. Electroactive Bacteria Associated With Stainless Steel Ennoblement in Seawater. *Frontiers in Microbiology* 10, doi:10.3389/fmicb.2019.00170 (2019).
10. Eddie, B. J. et al. '*Candidatus Tenderia electrophaga*', an uncultivated electroautotroph from a biocathode enrichment. *Int J Syst Evol Microbiol* 66, 2178-2185, doi: 10.1099/ijsem.0.001006 (2016).
11. Wang, Z. et al. A previously uncharacterized, nonphotosynthetic member of the Chromatiaceae is the primary $CO_2$-fixing constituent in a self-regenerating biocathode. *Appl. Environ. Microbiol.* 81, 699-712 (2015).
12. Leary, D. H. et al. Metaproteomic evidence of changes in protein expression following a change in electrode potential in a robust biocathode microbiome. *PROTEOMICS* 15, 3486-3496, doi:10.1002/pmic.201400585 (2015).
13. Eddie, B. J. et al. '*Candidatus Tenderia electrophaga*', an uncultivated electroautotroph from a biocathode enrichment. *Int. J Syst. Evol. Microbiol.* 66, 2178-2185, doi: 10.1099/ijsem.0.001006 (2016).
14. Malanoski, A. P. et al. Relative abundance of '*Candidatus Tenderia electrophaga*' is linked to cathodic current in an aerobic biocathode community. *Microbial Biotechnology* 11, 98-111, doi:doi:10.1111/1751-7915.12757 (2018).
15. Yates, M. D. et al. Toward understanding long-distance extracellular electron transport in an electroautotrophic microbial community. *Energy & Environmental Science* 9, 3544-3558, doi:10.1039/c6ee02106a (2016).
16. Eddie, B. J. et al. Metatranscriptomics Supports the Mechanism for Biocathode Electroautotrophy by "*Candidatus Tenderia electrophaga*". *mSystems* 2, doi: 10.1128/mSystems.00002-17 (2017).
17. Emerson, D. & Floyd, M. M. Enrichment and isolation of iron-oxidizing bacteria at neutral pH. *Methods Enzymol* 397, 112-123, doi:10.1016/S0076-6879(05)97006-7 (2005).
18. Bard, A. J. & Faulkner, L. R. *Electrochemical methods: fundamentals and applications*. 2nd edn, (Wiley, 2001).
19. Manz, W, Amann, R., Ludwig, W, Wagner, M. & Schleifer, K. H. Phylogenetic Oligodeoxynucleotide Probes for the Major Subclasses of Proteobacteria—Problems and Solutions. *Syst Appl Microbiol* 15, 593-600, doi:Doi 10.1016/S0723-2020(11)80121-9 (1992).
20. Neubauer, S. C., Emerson, D. & Megonigal, J. P. Life at the energetic edge: kinetics of circumneutral iron oxidation by lithotrophic iron-oxidizing bacteria isolated from the wetland-plant rhizosphere. *Appl Environ Microbiol* 68, 3988-3995 (2002).
21. Franklin, T. J., Snow, G. A. & Franklin, T. J. *Biochemistry and molecular biology of antimicrobial drug action*. 6th edn, (Springer, 2005).
22. Faimali, M. et al. Evidence of enzymatic catalysis of oxygen reduction on stainless steels under marine biofilm. *Biofouling* 27, 375-384, doi:10.1080/08927014.2011.576756 (2011).
23. Gartman, A. et al. Microbes Facilitate Mineral Deposition in Bioelectrochemical Systems. *Acs Earth Space Chem* 1, 277-287, doi:10.1021/acsearthspacechem.7b00042 (2017).
24. Ooka, H., McGlynn, S. E. & Nakamura, R. Electrochemistry at Deep-Sea Hydrothermal Vents: Utilization of the Thermodynamic Driving Force towards the Autotrophic Origin of Life. *ChemElectroChem* 6, 1316-1323, doi: 10.1002/celc.201801432 (2019).
25. Onderko, E. L. et al. Electrochemical Behavior of *Marinobacter atlanticus* strain CP1. *Frontiers in Energy Research Vol.* 7 Article 60. June 2019 DOI: 10.3389/fenrg.2019.00060 (2019).

What is claimed is:

1. An apparatus for studying electroautotrophy, comprising: a reactor vessel containing natural or artificial seawater; an unpoised working electrode immersed in the seawater; a reference electrode immersed in the seawater; a counter electrode immersed in the seawater; and an electroautotrophic biofilm living attached to the working electrode, wherein the biofilm comprises Ca. *Tenderia electrophaga*.

2. The apparatus of claim 1, further comprising a potentiostat operably connected to each of the electrodes.

3. The apparatus of claim 1, wherein the working electrode comprises graphite, carbon cloth, or indium tin oxide.

4. The apparatus of claim 1, wherein the biofilm is effective to perform carbon fixation without the need for external electrical power nor sunlight.

* * * * *